US00PP23406P2

(12) United States Plant Patent
Fitzgerald

(10) Patent No.: US PP23,406 P2
(45) Date of Patent: Feb. 19, 2013

(54) ***CAREX* PLANT NAMED 'EVERORO'**

(50) Latin Name: *Carex oshimensis*
Varietal Denomination: Everoro

(76) Inventor: Pat Fitzgerald, Stoneyford (IE)

( * ) Notice: Subject to any disclaimer, the term of this patent is extended or adjusted under 35 U.S.C. 154(b) by 117 days.

(21) Appl. No.: 13/068,823

(22) Filed: May 20, 2011

(51) Int. Cl.
*A01H 5/00* (2006.01)

(52) U.S. Cl. ..... Plt./384
(58) Field of Classification Search ..... Plt./384
See application file for complete search history.

*Primary Examiner* — June Hwu
(74) *Attorney, Agent, or Firm* — Penny J. Aguirre

(57) ABSTRACT

A new cultivar of *Carex oshimensis*, 'Everoro', characterized its foliage that is variegated with leaf centers that are golden yellow in color and wide margins that are dark green in color, its compact clump-forming growth habit, its ability to be readily propagated by rhizome division and basal cuttings, and its hardiness at least in U.S.D.A. Zones 6 to 9.

2 Drawing Sheets

Botanical classification: *Carex oshimensis.*
Varietal denomination: 'Everoro'.

CROSS REFERENCE TO A RELATED APPLICATION

This application is related to a patent for a plant derived from the same parentage that is entitled Carex Plant Named 'Everillo' (U.S. Plant Pat. No. 21,002).

BACKGROUND OF THE INVENTION

The present invention relates to a new and distinct cultivar of *Carex oshimensis* and will be referred to hereafter by its cultivar name, 'Everoro'. 'Everoro' is a new cultivar of perennial ornamental grass grown for container and landscape use, primarily in shaded exposures.

The new cultivar, 'Everoro' arose as a naturally occurring chimeral mutation of *Carex oshimensis* 'Evergold' (not patented). The Inventor discovered 'Everoro' in August of 2007 in a container at his nursery in Oldtown, Stoneyford, Co. Kilkenny, Republic of Ireland.

Asexual reproduction of the new cultivar was first accomplished by rhizome division in Oldtown, Stoneyford, Co. Kilkenny, Republic of Ireland in January of 2008 by the Inventor. The characteristics of this cultivar have been determined to be stable and are reproduced true to type in successive generations.

SUMMARY OF THE INVENTION

The following traits have been repeatedly observed and represent the characteristics of the new cultivar. The new *Carex* has not been observed under all possible environmental conditions. These attributes in combination distinguish 'Everoro' from all other selections of *Carex* known to the Inventor.

1. 'Everoro' exhibits foliage that is variegated with leaf centers that are golden yellow in color and wide margins that are dark green in color.
2. 'Everoro' exhibits a plant habit that slowly spreads by rhizomes and forms compact clumps as it matures.

3. 'Everoro' is readily propagated by rhizome division and basal cuttings.
4. 'Everoro' is hardy at least in U.S.D.A. Zones 6 to 9.

'Everoro' has a similar plant habit and growth rate to its parent plant, 'Evergold', however 'Everoro' exhibits leaves that have wider margins that are darker green in color and leaf centers that are deeper gold in color. 'Everoro' can be most closely compared to the cultivars 'Carfit01' also known as 'Everest' (U.S. Plant Pat. No. 20,955) and 'Everillo'(U.S. Plant Pat. No. 21,002). 'Everest' differs from 'Everoro' in having foliage with leaf centers that are green in color rather than golden in color. 'Everillo' differs from 'Everoro' in having leaves that lack variegation and are solid gold in color.

BRIEF DESCRIPTION OF THE DRAWING

The accompanying colored photographs illustrate the overall appearance and distinct characteristics of six month-old plants as grown in 10-cm containers outdoors in Oldtown, Stoneyford, C. Kilkenny, Ireland.

The photograph in FIG. 1 illustrates the overall plant habit and appearance of 'Everoro'.

Figure 1:
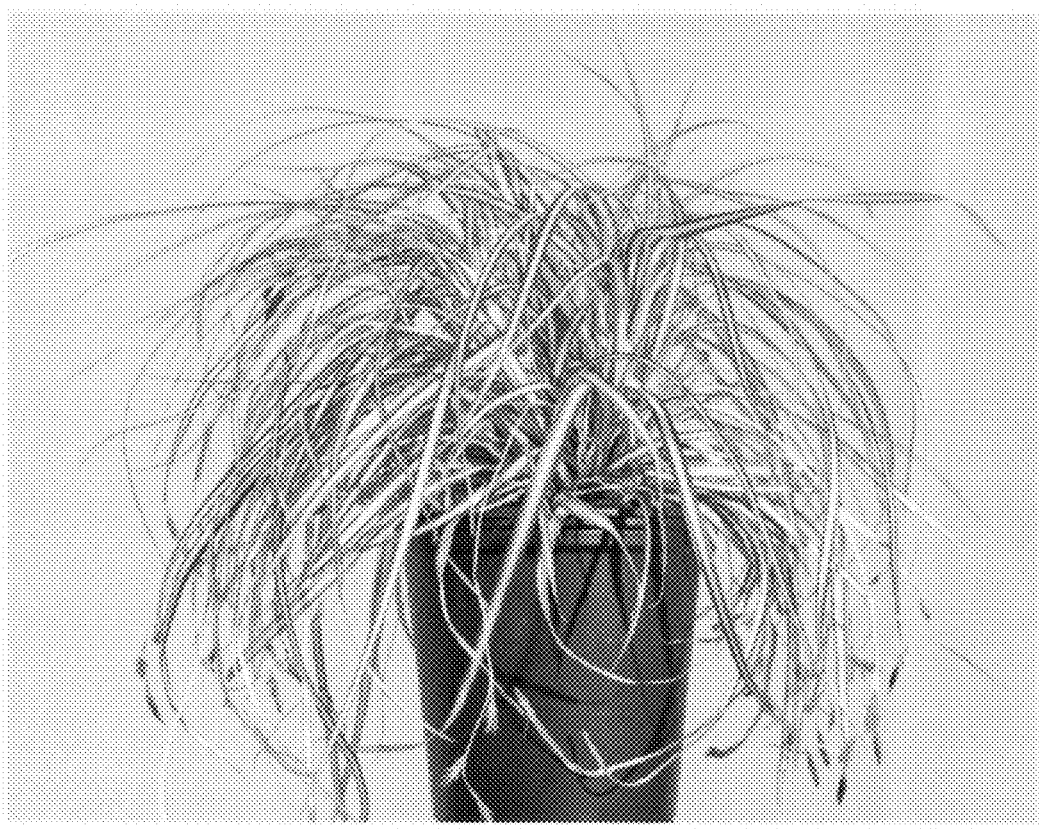
Figure 2:
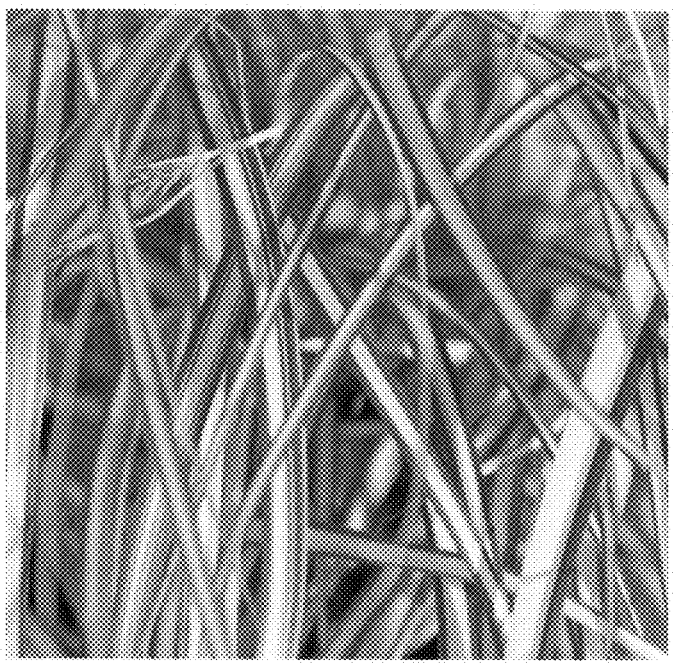

The photograph in FIG. 2 provides a detailed close-up view of the leaf coloration and variegation pattern of 'Everoro'.

Figure 3:
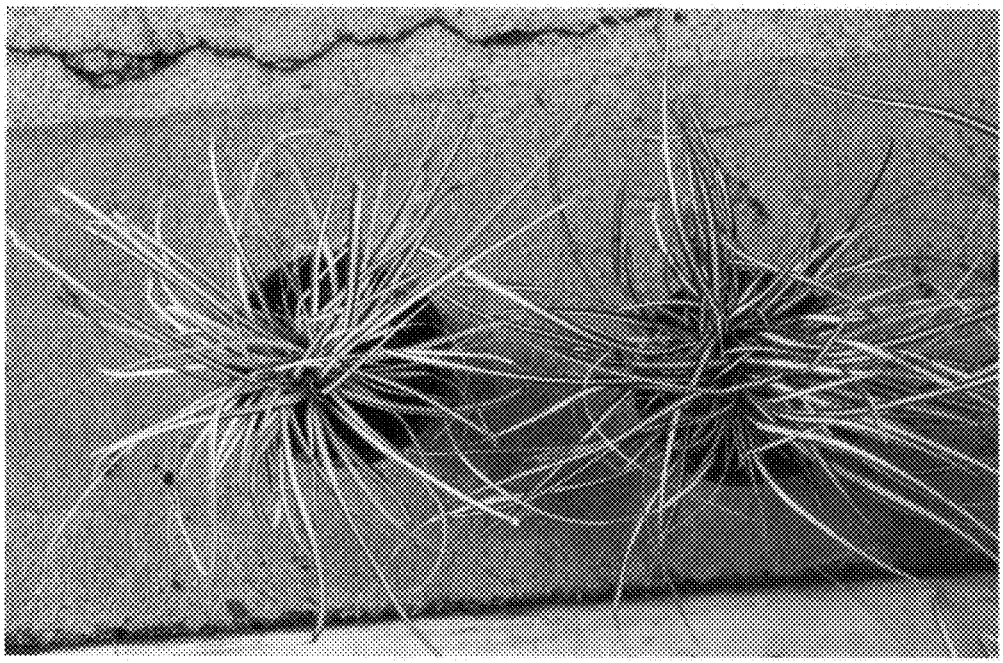

The photograph in FIG. 3 shows a comparison between 'Evergold' on the left and 'Everoro' on the right. The colors in the photograph may differ slightly from the color values cited in the detailed botanical description, which accurately describe the colors of the new *Carex*.

DETAILED BOTANICAL DESCRIPTION

The general observations and descriptions describe plants of 'Everoro' as grown in a greenhouse in 10-cm containers in Co. Kilkenny, Republic of Ireland for six months from a single rhizome division. Plants were grown under average day temperature of 12° to 22° C. and average night temperatures of 8° to 18° C. The phenotype may vary somewhat with variations in temperature, day-length, light intensity, soil types, and water and fertility levels without, however, any variance in genotype. The color determinations are in accordance with The 2007 R.H.S. Colour Chart of The Royal Horticultural Society, London, England, except where general color terms of ordinary dictionary significance are used.

General description:

*Blooming period*.—Inflorescences emerge in January and continue into summer in the Republic of Ireland.

*Plant habit*.—Herbaceous clump-forming ornamental perennial grass, evergreen at least to U.S.D.A. Zone 6, flattened-globular mound in shape.

*Growth habit*.—Broadly spreading.

*Height and spread*.—Reaches about 14.6 cm in height, spreads to about 32.2 cm in diameter.

*Hardiness*.—At least in U.S.D.A. Zones 6 to 9.

*Culture*.—Grows best in part shade in fertile, well-drained soils with adequate moisture, tolerant to full shade in warmer climates and full sun in cooler climates.

*Diseases and pests*.—No increased susceptibility or resistance to diseases or pests has been observed.

*Root description*.—Short, stout rhizomes with dense, fibrous roots, roots moderately branched.

Growth and propagation:

*Propagation*.—Rhizome division and basal cuttings.

*Root initiation from cuttings*.—About 4 weeks at 20° C. day temperatures and produce fully rooted liner in about 3 months.

*Root development from division*.—Fully develop in 10-cm containers in about 9 months from rhizome divisions.

*Growth rate*.—Moderate.

*Branching*.—Main shoots grow from the base, no lateral branches.

Foliage description:

*Leaf shape*.—Linear, strongly curved.

*Leaf division*.—Simple.

*Leaf base*.—Sheathed.

*Leaf apex*.—Long acuminate.

*Leaf aspect*.—Leaves initially emerge upright, then cascade outward and finally arch downward until the terminal blades lay on the ground.

*Leaf venation*.—Parallel, color matches leaf color.

*Leaf margins*.—Entire, slightly scaberulose.

*Leaf persistence*.—Persistent; evergreen under conditions tested.

*Leaf size*.—Average of 20.4 cm in length and 6 mm in width.

*Leaf number*.—Average of 7 leaves per shoot, about 34 shoots in a 10-cm container.

*Leaf arrangement*.—Alternate.

*Leaf surface*.—Moderately glossy and smooth.

*Leaf durability to stress*.—High.

*Leaf color*.—Young leaves upper surface; center ranges from 4D and 8D, margins range from 143B to 144A, mature leaves upper surface; center ranges from 5D to 6D, margins between 137A and 143A, base 4D with lighter margins 144B, young leaves lower surface; center ranges from 4D and 8D, margins range from 143B to 143C, mature leaves lower surface; center ranges from 5D to 6D, margins range from 137A to 137B, base 4D with lighter margins ranging from 143B to 144A to 144B.

Flower description:

*General description*.—Terminal racemes, male and female flowers in separate spikelets.

*Inflorescence size*.—Averages 3.7 cm in height and 7 mm in width.

*Flower quantity per inflorescence*.—Typically 60 male flowers placed in an average of 1 spikelet and an average of 70 female flowers placed in an average of 2 spikelets.

*Lastingness of inflorescence*.—Flowers last about 10 days.

*Flowering season*.—Late winter into summer.

*Response time to flower*.—Approximately 8 months.

*Rate of flower opening*.—After first initial flowers open in an inflorescence all flowers open within 3 weeks.

*Fragrance*.—None.

*Floret buds*.—Narrowly ovate in shape, about 1.9 cm in length and about 2 mm in diameter, range from 165C to 165D in color.

*Spikelet aspect*.—Upright to outward.

*Spikelet shape*.—Sedge-like.

*Persistence of spikelets*.—Persistent.

*Floret (spikelet) size*.—Staminate florets; an average of 4 mm in diameter and 1 cm in length, pistillate florets; an average of 2 mm in diameter.

*Floret (spikelet) description*.—1 glume on outer side and 1 lemma on inner side on staminate florets and 1 lemma on inner side of pistillate florets (lack glumes), glumes; an average of 4 mm in length and 1 mm in width, lanceolate in shape, margin entire, apex narrowly acute, color of upper and lower surface 164A, surface is smooth and dull in appearance, lemma; an average of 2 mm in length and 0.5 mm in width, lanceolate in shape, margin entire, apex long and mucronate, color of upper and lower surface on staminate florets 164A, color of upper and lower surface on pistillate florets 161A, surface is smooth and dull in appearance.

*Peduncle*.—An average of 13.8 cm in length and 1 mm in diameter, strong, held upright from center of shoot at average angle 0°, secondary peduncles average angle of 5°, 162D in color.

Reproductive organs:

*Gynoecium*.—Average of 3 pistils about 0.7 mm in length, stigma is fimbriate and 197C in color, style is about 0.1 mm in length, insufficient in size to be color coded, ovary is 157A in color.

*Androcoecium*.—Average of 3 stamens, basifixed, about 2 mm in length and ranges from 164A to 164B in color, pollen production very low and insufficient in quantity to be color coded.

*Fruits and seeds*.—Seed production has not been observed to date.

It is claimed:

1. A new and distinct cultivar of *Carex* plant named 'Everoro' as herein illustrated and described.

* * * * *